United States Patent
Hähnle et al.

(10) Patent No.: US 6,800,666 B2
(45) Date of Patent: Oct. 5, 2004

(54) HYDROPHILIC, OPEN-CELL, ELASTIC FOAMS WITH A MELAMINE/FORMALDEHYDE RESIN BASE, PRODUCTION THEREOF AND USE THEREOF IN HYGIENE PRODUCTS

(75) Inventors: Hans-Joachim Hähnle, Neustadt (DE); Horst Baumgartl, Ludwigshafen (DE); Martin Beck, Maxdorf (DE); Norbert Herfert, Altenstadt (DE); Bernhard Mohr, Heidelberg (DE); Jürgen Huff, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 28 days.

(21) Appl. No.: 10/380,457

(22) PCT Filed: Sep. 20, 2001

(86) PCT No.: PCT/EP01/10848
§ 371 (c)(1), (2), (4) Date: Mar. 10, 2003

(87) PCT Pub. No.: WO02/26871
PCT Pub. Date: Apr. 4, 2002

(65) Prior Publication Data
US 2004/0097609 A1 May 20, 2004

(30) Foreign Application Priority Data
Sep. 27, 2000 (DE) .......................... 100 47 717

(51) Int. Cl.$^7$ .............................. C08J 9/224; C08J 9/28; A61F 13/15
(52) U.S. Cl. .......................... 521/64; 521/50.5; 521/57; 604/358; 604/369
(58) Field of Search .................. 521/64, 50.5, 573; 604/358, 369

(56) References Cited

U.S. PATENT DOCUMENTS

| 4,334,971 A | 6/1982 | Mahnke et al. |
| 4,511,678 A | 4/1985 | Mahnke et al. |
| 4,540,717 A | 9/1985 | Mahnke et al. |
| 4,666,948 A | 5/1987 | Woerner et al. |
| 5,292,777 A | 3/1994 | DesMarais et al. |
| 5,318,554 A | 6/1994 | Young et al. |
| 5,550,167 A | 8/1996 | DesMarais |

FOREIGN PATENT DOCUMENTS

| DE | 31 38 862 | 5/1982 |
| DE | 100 27 770 | 12/2001 |
| EP | 0 017 621 | 12/1982 |
| EP | 0 017 672 | 4/1983 |
| EP | 0 037 470 | 6/1985 |
| EP | 0 220 506 | 5/1987 |
| WO | WO 96/21682 | 7/1996 |
| WO | WO 97/07832 | 3/1997 |
| WO | WO 00/19436 | 4/2000 |

Primary Examiner—Morton Foelak
(74) Attorney, Agent, or Firm—Marshall, Gerstein & Borun LLP

(57) ABSTRACT

Hydrophilic open-celled resilient foams containing melamine-formaldehyde resins, characterized by a droplet absorption rate of less than 5 seconds and an EU standard EN ISO 14184-1 formaldehyde emission of less than 100 mg of formaldehyde/kg of foam, and obtainable by (a) heating an aqueous solution or dispersion each containing at least a melamine-formaldehyde precondensate, an emulsifier, a blowing agent and a curing agent to form a foam and crosslink the precondensate, (b) then conditioning the foam at from 120 to 300° C. for from 1 to 180 minutes to remove volatiles, and (c) treating the foam during the conditioning or thereafter with at least one hydrophilicizer and/or with ozone, a corona discharge or a plasma, are useful in hygiene articles to acquire, distribute and immobilize body fluids.

14 Claims, No Drawings

HYDROPHILIC, OPEN-CELL, ELASTIC FOAMS WITH A MELAMINE/ FORMALDEHYDE RESIN BASE, PRODUCTION THEREOF AND USE THEREOF IN HYGIENE PRODUCTS

CROSS REFERENCE TO RELATED APPLICATION

This is the U.S. national phase application of International Application No. PCT/EP01/10848, filed Sep. 20, 2001.

The present invention relates to hydrophilic open-celled resilient foams based on melamine-formaldehyde resins, their preparation and their use in hygiene articles.

EP-A-0 017 621 and EP-A-0 017 672 disclose open-celled resilient foams based on melamine-formaldehyde condensation products and to processes for their preparation. The process known from EP-A-0 037 470 produces open-celled resilient foams from melamine-formaldehyde condensation products in a particularly advantageous manner by the action of microwave energy (ultrahigh frequency irradiation) on an aqueous solution or dispersion each containing a melamine-formaldehyde precondensate, an emulsifier, a blowing agent and a curing agent. The solution or dispersion is heated in such a way that it foams up and cures the precondensate. The foams thus obtainable emit small amounts of formaldehyde at a rate which increases with increasing foam temperature and moisture content.

The construction of hygiene articles and use of open-celled foams of melamine-formaldehyde resins as absorbent interlayer are extensively described in prior DE application no. 100 34 505.0, unpublished at the priority date of the present invention. The melamine-formaldehyde resin foams recited therein are highly hydrophilic, but they give off a comparatively large amount of formaldehyde on contact with body fluids. This substantially limits the possibility of using such foams in hygiene articles.

Prior DE application no. 100 27 770.5, unpublished at the priority date of the present invention, describes the preparation of foams from low-formaldehyde open-celled melamine-formaldehyde resins having a molar ratio of melamine to formaldehyde in the range from 1:1.0 to 1:1.9. These foams emit less than 30 mg of formaldehyde per kg of foam even under the warm-moist conditions customary in the hygiene sector (EU standard EN ISO 14 184-1, water immersion at 40° C. for 1 h). They consequently meet the baby clothing requirements of Oeko-Tex Standard 100 (quality mark of textiles tested for harmful substances). However, the appreciable reduction in formaldehyde emission comes at the expense of a partial loss of hydrophilic properties of the foam, as a result of which the liquid acquisition rate of such foam layers decreases.

WO-A-96/21682 discloses foams which, owing to their open-celled structure, are very useful for absorbing aqueous body fluids, especially blood. The foams are obtained by polymerization of ($C_4$–$C_{14}$)alkyl acrylates, ($C_6$–$C_{16}$)alkyl methacrylates, ($C_4$–$C_{12}$)alkylstyrenes as monomers, preferably styrene and ethylstyrene as comonomers, also aromatic polyvinyl compounds as crosslinkers; optionally polyfunctional acrylates, methacrylates, acrylamides and methacrylamides and mixtures thereof as additional cross-linker substances. The polymerization takes place within a High Internal Phase Emulsion (HIPE) of the W/O type in which the weight ratio of water phase to oil phase is in the range from 20:1 to 125:1. After the polymerization has ended, the polymer foams are washed and dried.

WO-A-97/07832, U.S. Pat. Nos. 5,318,554 and 5,550,167 concern the production of open-celled foams based on HIPE emulsions and their use in hygiene articles to absorb aqueous body fluids. However, the open-celled foams are always used together with other components responsible for ultimate absorption (immobilization) of the body fluids. The materials have good application advantages, but also clear disadvantages. For instance, the production of these materials is an extremely complicated process which is difficult to control. The enormous amount of aqueous phase (aqueous salt solution) required is neither economically nor ecologically sensible. Moreover, the materials are hydrophilicized at the surface with a salt layer. This layer can become detached during use and wash into the storage medium of the absorbent core. The storage medium is generally made of superabsorbents. It is known that superabsorbents are susceptible to "salt poisoning," i.e., their absorbency decreases dramatically with the increasing salt content of the solution to be absorbed. It is therefore certainly not desirable to additionally increase the salt load in the body fluids to be absorbed.

It is an object of the present invention to provide open-celled resilient foams based on melamine-formaldehyde resins that are hydrophilic and whose formaldehyde emissions are substantially reduced compared to existing foams of melamine-formaldehyde resins.

We have found that this object is achieved by hydrophilic open-celled resilient foams comprising melamine-formaldehyde resins, characterized by a droplet absorption rate of less than 5seconds and an EU standard EN ISO 14184-1 formaldehyde emission of less than 100 mg of formaldehyde/kg of foam.

Such foams have, for example, a density of from 5 to 200 g/l, a specific surface area (determined according to BET) of more than 0.5 $m^2$/g and a Free Swell Capacity of more than 20 g/g. They have, for example, in the wet state a tensile strength of >60 $J/m^2$.

The invention also provides a process for preparing hydrophilic open-celled resilient foams, which comprises (a) heating an aqueous solution or dispersion each containing at least a melamine-formaldehyde precondensate, an emulsifier, a blowing agent and a curing agent to form a foam and crosslink the precondensate, (b) then conditioning the foam at from 120° C. to 300° C. for from 1 to 180 minutes to remove volatiles, and (c) treating the foam during the conditioning or thereafter with at least one hydrophilicizer and/or with ozone, a corona discharge or a plasma.

Process step (a) is known from the prior art, cf. the above-discussed references EP-A-0 017 621, EP-A-0 017 672 and EP-A-0 037 470. The molar ratio of melamine to formaldehyde is, for example, in the range from 1:1.0 to 1:5 and is preferably in the range from 1:1.0 to 1:1.9. The preferred range is known from prior DE application no. 100 27 770.5, unpublished at the priority date of the present invention. To produce low-formaldehyde and melamine-formaldehyde resins it is particularly advantageous for the molar ratio of melamine to formaldehyde to be within the range from 1:1.3 to 1:1.8. The foaming as per step (a) is effected by heating the mixture to a temperature above the boiling point of the blowing agent and is carried out, for example, in such a way that initially there is little increase in the viscosity and a steep rise in the viscosity and crosslinking substantially does not occur until the foaming process has ended. However, foaming of the mixture and crosslinking of the precondensate may also be effected concurrently. Heating of the mixture is effected, for example, using hot air or steam and/or by utilizing heat of reaction. The foaming of the aqueous mixture of melamine-formaldehyde precondensate, emulsifier, blowing agent and curing agent is preferably effected by means of microwaves "by the action of microwave energy" according to the process known from EP-A-0 037 470.

Structure and mechanical properties of the foams are known from EP-A-0 017 672:

The DIN 53 420 density is in the range from 1.6 to 30, preferably from 2 to 20 [g/l];

the DIN 52 612 coefficient of thermal conductivity is less than 0.06, preferably less than 0.04 [$W.m^{-1}.K^{-1}$];

the DIN 53 577 compression hardness on 60% compression, divided by the density, is less than 0.3, preferably less than 0.2 [$N.cm^{-2}/g.l^{-1}$], the determination of the compression hardness at 60% compression having to be followed by a recovery of the foam to at least 70%, preferably at least 90%, especially 95%, of its original dimensions;

the modulus of elasticity on the lines of DIN 53 423, divided by the density, is less than 0.25, preferably less than 0.15 [$N.mm^{-2}/g.l^{-1}$].

the DIN 53 423 bending travel on fracture is more than 10, preferably more than 15 [mm];

the DIN 53 527 compression set on 50% compression is less than 45%, preferably less than 30%, especially less than 10%;

the DIN 18 165 dynamic stiffness for a sheet thickness of 50 mm is less than 20, preferably less than 10, especially less than 5 [$N.cm^{-3}$];

under DIN 4102 they have at most normal flammability, preferably low flammability;

tensile strength in the wet state >60 $J/m^2$;

BET surface area of foam >0.5 $m^2/g$.

The foams which are based on melamine-formaldehyde condensation products and which are used according to the invention are open-pored. Under the microscope, the foam structure is seen to contain a multiplicity of interconnected, three-dimensionally branched webs. Melamine-formaldehyde resin foams are sufficiently resilient only when the webs meet the conditions described in EP-A-0 017 672, i.e., the average ratio of web length to web thickness is greater than 10:1, preferably greater than 12:1, especially greater than 15:1, and web density is more than 1.10, preferably more than 1.20, especially more than 1.30 $g/cm^3$. Web length and thickness is determined under the microscope, for example, and the density of the foam webs is determined according to Archimedes' principle by dipping the foams into a suitable liquid such as isopropanol, see EP-A-0 017 672.

In process step (b), the foam is conditioned at from 120° C. to 300° C. for from 1 to 180 minutes. It is heated to a temperature in the range from 120° C. to 260° C., particularly preferably in the range from 150° C. to 250° C., for from preferably 3 minutes to 60 minutes, substantially removing water, blowing agent and formaldehyde and supplementarily curing the foam resin. This heat treatment may be carried out immediately following foam production in the same apparatus or in a downstream apparatus; but it can also be carried out at a later time independently of the foaming process. Conditioned foams are substantially less prone to shrinkage and have a lower equilibrium moisture content than products which have not been conditioned. Formaldehyde emissions are similarly substantially reduced compared to the formaldehyde emissions of unconditioned products. Formaldehyde detachment is less than 100 mg of formaldehyde/kg of foam, preferably less than 20 mg of formaldehyde/kg of foam (measured according to EU standard ISO 14184-1).

The foams can be produced as sheets, blocks or webs up to 2 m in height or as films a few mm in thickness, for example, in the range from 0.5 to 7 mm. The preferred foam height (in the foam rise direction) is in the range from 10 cm to 100 cm for 2.45 GHz microwaves. All desired sheet or fleece thicknesses can be cut out of such foam blocks.

To increase the absorption rate of the foams for water and body fluids, they are hydrophilicized in process step (c). The hydrophilicization may also be carried out during the conditioning, for example, by having hot air flow through the melamine-formaldehyde resin foam to remove all volatiles and adding hydrophilicizing substances, for example, in the form of an aerosol to this conditioning air. This makes it possible to obtain a hydrophilicization without the foams having to be subsequently treated with a hydrophilicizer.

The generation of the necessary hydrophilicity in process step (c) can be effected in various ways, for example, by treatment with at least one hydrophilicizer and/or ozone, a corona discharge or a plasma.

When the foam is treated with a hydrophilicizer, this may take the form, for example, of an adsorption of a more hydrophilic component, for example, of surfactants or hydrophilic polymers, which optionally exhibit a hydrophobic modification, or a chemical attachment of hydrophilic reagents, for example, of polyamines, polyepoxides or polycarboxylic acids on the surface of the foam. Hydrophilicization of the surface of the foam may also be effected by applying crosslinked polymers or a crosslinked hydrophilic sheath, for example, by having reagents capable of forming a network with themselves such as condensation products of epichlorohydrin and polyamidoamines or polyamines or monomers or polymers capable of reacting with an added crosslinker, for example, polycarboxylic acids in combination with multifunctional epoxides, polyhydric alcohols or polyamines, polyamines in combination with multifunctional epoxides, acrylates or esters act on the foams. The hydrophilicizers are normally employed in dissolved form by dissolving them in a solvent. They may also be applied in the form of aqueous dispersions or dispersions in an organic solvent to the foams to be hydrophilicized. The hydrophilicization may be effected, for example, by dipping the melamine-formaldehyde foam body into the liquid which contains the hydrophilicizer in dissolved or in dispersed form. Alternatively the liquid with the dissolved or dispersed hydrophilicizer may also be sprayed on the foam surface. The solvent is thereafter removed from the hydrophilicized foam body, for example, by drying the foam.

The hydrophilicizer reacts with the melamine-formaldehyde resin foam to be hydrophilicized and is adsorbed at the polymer surfaces. The amount of hydrophilicizer added is dimensioned in such a way that, on the one hand, a hydrophilicization is brought about without, on the other hand, disrupting the mechanical properties of the foam (flexibility). Preferably the hydrophilicizer is added in such an amount that the resulting amount of hydrophilicizer is in the range from 0.05 to 100% by weight preferably in the range from 0.1 to 50% by weight, especially in the range from 0.2 to 30% by weight, based on the foam.

Hydrophilicization of the melamine-formaldehyde foam is possible, for example, through the action of at least one surfactant on the foam. Particular preference is given to adding skin-friendly surfactants. Examples of skin-friendly hydrophilicizers are oil-soluble surfactants such as sorbitan fatty acid esters, polyglycerol fatty acid esters and polyoxyethylene. Examples of surfactants of the above type are TRIODAN® 20, a commercially available polyglycerol ester, and EMSORB® 2502, a sorbitan sesquioleate. Preferred sorbitan fatty acid esters are sorbitan laurate (e.g., SPAN® 20), sorbitan monooleate (SPAN® 80) and combinations of sorbitan trioleate (SPAN® 85) and sorbitan monooleate (SPAN® 80). Particular preference is given to the combination of sorbitan monooleate and sorbitan trioleate in a weight ratio of not less than 3:1, particularly preferably of 4:1. Combinations of sorbitan laurate with certain polyglycerol fatty acid esters are also used as hydrophilicizers. Polyglycerol fatty acid esters are obtained from ester-forming polyglycerols and fatty acids, cf., for example, U.S. Pat. No. 3,637,774. Polyglycerols are characterized by a high fraction of linear (especially acyclic) diglycerols, a low fraction of tri- or higher polyglycerols and a low fraction of cyclic diglycerols. The weight ratio of sorbitan laurate to polyglycerol fatty acid ester is normally in the range from 10:1 to 1:10, preferably in the range from 4:1 to 1:1.

Preference is further given to organomodified polydimethylsiloxanes of the type NUWET® 500 or modified silicones of the type NUWET® 300 (from OSi) Both the polydimethylsiloxanes and the polysilicones are modified to be hydrophilic. This modification may be effected through the incorporation of amino, carboxyl or hydroxyl groups. It is likewise possible to attach oligo- or polyethylene glycol side chains.

Useful hydrophilicizers further include acylated polyamines, obtainable, for example, by reaction of polyamines with monobasic carboxylic acids. Useful polyamines include, for example, polyalkylenepolyamines having average molar masses of from 300 to 1 million, preferably of from 500 to 500,000. Preferred polyalkylenepolyamines are polyethyleneimines.

The monobasic carboxylic acids usually have from 1 to 18 carbon atoms, for example, formic acid, acetic acid, propionic acid, lauric acid, palmitic acid or stearic acid. In some cases it is advantageous to react mixtures of a long-chain monocarboxylic acid in succession or together with a polyalkylenepolyamine. Instead of carboxylic acids it is also possible to use the esters of carboxylic acids. When the polyalkylenepolyamines are reacted with the carboxylic acids or esters, the $NH_2$ or NH groups of the polyalkylenepolyamines are amidated. This is a way of acylating, for example, from 5 to 100%, preferably from 15 to 85%, of the nitrogen atoms in the polyalkylenepolyamine.

Useful hydrophilicizers further include polymers containing i) at least one polyisocyanate and
ii) at least one compound having at least two isocyanate-reactive groups and additionally at least one tertiary amino group in built-in form. At least some of the tertiary amino groups of component ii) in the polymer are in the form of ammonium groups. Charged cationic groups can be produced from the tertiary amine nitrogens of the compounds of component ii) and/or of the polymer either by protonation or by quaternization. Then at least a portion of the tertiary amino groups in the polymer will be present in the form of its reaction products with at least one neutralizing (protonating) and/or quaternizing agent.

The polyisocyanates i) are preferably selected from compounds having from 2 to 5 isocyanate groups, isocyanate prepolymers having an average number of from 2 to 5 isocyanate groups and mixtures thereof. It is also possible to use compounds which in addition to or instead of free isocyanate groups have functional groups which release isocyanate groups or react like isocyanate groups. These include, for example, compounds having blocked isocyanate groups, uretdione groups, isocyanurate groups and/or biuret groups. The compounds having isocyanurate groups are in particular simple triisocyanatoisocyanurates, i.e., cyclic trimers of diisocyanates, or mixtures with their higher homologs having more than one isocyanurate ring. Useful compounds of component ii) further include, for example, tertiary amines where the amine nitrogen has three substituents, which are preferably hydroxyalkyl and/or aminoalkyl groups. Preferred compounds used for component ii) are, for example, bis(aminopropyl)methylamine, bis(aminopropyl)piperazine, methyldiethanolamine and mixtures thereof.

Useful cationic polymers include all cationic synthetic polymers containing amino and/or ammonium groups. Examples of such cationic polymers are vinylamine polymers, vinylimidazole polymers, polymers containing quaternary vinylimidazol units, condensates of imidazole and epichlorohydrin, crosslinked polyamidoamines, ethyleneimine-grafted crosslinked polyamidoamines, polyethyleneimines, alkoxylated polyethyleneimines, crosslinked polyethyleneimines, amidated polyethyleneimines, alkylated polyethyleneimines, polyamines, amine-epichlorohydrin polycondensates, water-soluble polyaddition products of multifunctional amines with multifunctional epoxides, alkoxylated polyamines, polyallylamines, polydimethyldiallylammonium chlorides, polymers containing basic (meth)acrylamide or (meth)acrylic ester units, polymers containing basic quaternary (meth)acrylamide or (meth)acrylic ester units, and/or lysine condensates.

Cationic polymers also include amphoteric polymers having a net cationic charge, i.e., the polymers contain not only anionic but also cationic monomers in polymerized form, but the molar fraction of cationic units contained in the polymer is larger than that of the anionic units.

Vinylamine polymers (i.e., polymers containing vinylamine units) are preparable, for example, from open-chain N-vinylcarboxamides of the formula

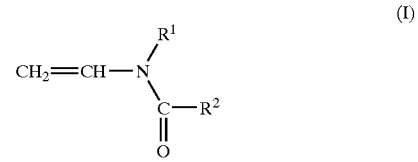

(I)

where $R^1$ and $R^2$ are identical or different and are each hydrogen or $C_1$- to $C_6$-alkyl. Useful monomers include, for example, N-vinylformamide ($R^1=R^2=H$ in formula I), N-vinyl-N-methylformamide, N-vinylacetamide, N-vinyl-N-methylacetamide, N-vinyl-N-ethylacetamide, N-vinyl-N-methylpropionamide and N-vinylpropionamide. To prepare the polymers, the monomers mentioned may be polymerized alone, mixed with each other or together with other monoethylenically unsaturated monomers. Homo- and copolymers of N-vinylformamide are preferred as starting materials. Vinylamine polymers are known, for example, from U.S. Pat. No. 4,421,602, U.S. Pat. No. 5,334,287, EP-A-0 216 387 and EP-A-0 251 182. They are obtained by acid, base or enzymatic hydrolysis of polymers containing units derived from monomers of the formula I.

Useful monoethylenically unsaturated monomers for copolymerization with N-vinylcarboxamides include all compounds copolymerizable therewith. Examples thereof are vinyl esters of saturated carboxylic acids of from 1 to 6 carbon atoms such as vinyl formate, vinyl acetate, vinyl propionate and vinyl butyrate and vinyl ethers such as $C_1$- to $C_6$-alkyl vinyl ethers, e.g., methyl or ethyl vinyl ether. Useful comonomers further include ethylenically unsaturated $C_3$- to $C_6$-carboxylic acids, for example, acrylic acid, methacrylic acid, maleic acid, crotonic acid, itaconic acid and vinylacetic acid and also their alkali metal and alkaline earth metal salts, esters, amides and nitriles of the carboxylic acids mentioned, for example, methyl acrylate, methyl methacrylate, ethyl acrylate and ethyl methacrylate.

Further useful carboxylic esters are derived from glycols or polyalkylene glycols where in each case only one OH group is esterified, for example, hydroxyethyl acrylate, hydroxyethyl methacrylate, hydroxypropyl acrylate, hydroxybutyl acrylate, hydroxypropyl methacrylate, hydroxybutyl methacrylate and also monoacrylate esters of polyalkylene glycols having a molar mass of from 500 to 10,000. Useful comonomers further include esters of ethylenically unsaturated carboxylic acids with aminoalcohols, for example, dimethylaminoethyl acrylate, dimethylaminoethyl methacrylate, diethylaminoethyl acrylate, diethylaminoethyl methacrylate, dimethylaminopropyl acrylate, dimethylaminopropyl methacrylate, diethylaminopropyl acrylate, dimethylaminobutyl acrylate and diethylaminobutyl acrylate. Basic acrylates can be used in the form of the free bases, the salts with mineral acids such as hydrochloric acid, sulfuric acid or nitric acid, the salts with organic acids such as formic acid, acetic acid, propionic acid or sulfonic acids or in quaternized form. Useful quaternizing agents include, for example, dimethyl sulfate, diethyl sulfate, methyl chloride, ethyl chloride or benzyl chloride.

Useful comonomers further include amides of ethylenically unsaturated carboxylic acids such as acrylamide, methacrylamide and also N-alkylmonoamides and diamides of monoethylenically unsaturated carboxylic acids with alkyl radicals of from 1 to 6 carbon atoms, for example, N-methylacrylamide, N,N-dimethylacrylamide, N-methylmethacrylamide, N-ethylacrylamide and N-propylacrylamide and tert-butylacrylamide and also basic (meth)acrylamides, for example, dimethylaminoethylacrylamide, dimethylaminoethylmethacrylamide, diethylaminoethylacrylamide, diethylaminoethylmethacrylamide, dimethylaminopropylacrylamide, diethylaminopropylacrylamide, dimethylaminopropylmethacrylamide and diethylaminopropylmethacrylamide.

Useful comonomers further include N-vinylpyrrolidone, N-vinylcaprolactam, acrylonitrile, methacrylonitrile, N-vinylimidazole and also substituted N-vinylimidazoles, for example, N-vinyl-2-methylimidazole, N-vinyl-4-methylimidazole, N-vinyl-5-methylimidazole, N-vinyl-2-ethylimidazole and N-vinylimidazolines such as N-vinylimidazoline, N-vinyl-2-methylimidazoline and N-vinyl-2-ethylimidazoline. N-Vinylimidazoles and N-vinylimidazolines are used not only in the form of the free bases but also after neutralization with mineral acids or organic acids or after quaternization, a quaternization being preferably effected with dimethyl sulfate, diethyl sulfate, methyl chloride or benzyl chloride. Also useful are diallyldialkylammonium halides, for example, diallyldimethylammonium chlorides.

Useful comonomers further include sulfo-containing monomers, for example, vinylsulfonic acid, allylsulfonic acid, methallylsulfonic acid, styrenesulfonic acid, the alkali metal or ammonium salts of these acids or 3-sulfopropyl acrylate. Since the amphoteric copolymers contain more cationic units than anionic units, they have a cationic charge overall.

The copolymers contain, for example
  from 99.99 to 1 mol %, preferably from 99.9 to 5 mol %, of N-vinylcarboxamides of the formula I and
  from 0.01 to 99 mol %, preferably from 0.1 to 95 mol %, of other monoethylenically unsaturated monomers copolymerizable therewith
in copolymerized form.

To prepare vinylamine polymers it is preferable to start from homopolymers of N-vinylformamide or from copolymers obtainable by copolymerization of
  N-vinylformamide with
  vinyl formate, vinyl acetate, vinyl propionate, acrylonitrile, N-vinylcaprolactam, N-vinylurea, acrylic acid, N-vinylpyrrolidone or $C_1$- to $C_6$-alkyl vinyl ethers
  and subsequent hydrolysis of the homo- or copolymers to form vinylamine units from the copolymerized N-vinylformamide units, the degree of hydrolysis being, for example, in the range from 0.1 to 100 mol %.

The hydrolysis of the above-described polymers is effected according to known processes by the action of acids, bases or enzymes. This converts the copolymerized monomers of the above-indicated formula I through detachment of the group

(II)

where $R^2$ is as defined for formula I, into polymers which contain vinylamine units of the formula

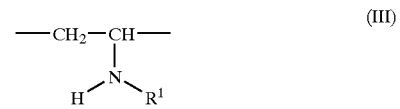

(III)

where $R^1$ is as defined for formula I. When acids are used as hydrolyzing agents, the units III are present as ammonium salt.

The homopolymers of the N-vinylcarboxamides of the formula I and their copolymers may be hydrolyzed to an extent in the range from 0.1 to 100 mol %, preferably to an extent in the range from 70 to 100 mol %. In most cases, the degree of hydrolysis of the homo- and copolymers is in the range from 5 to 95 mol %. The degree of hydrolysis of the homopolymers is synonymous with the vinylamine units content of the polymers. In the case of copolymers containing units derived from vinyl esters, the hydrolysis of the N-vinylformamide units can be accompanied by a hydrolysis of the ester groups with the formation of vinyl alcohol units. This is the case especially when the hydrolysis of the copolymers is carried out in the presence of aqueous sodium hydroxide solution. Copolymerized acrylonitrile is likewise chemically modified in the hydrolysis, for example, converted into amide groups or carboxyl groups. The homo- and copolymers containing vinylamine units may optionally contain up to 20 mol % of amidine units, formed, for example, by reaction of formic acid with two adjacent amino groups or by intramolecular reaction of an amino group with an adjacent amide group, for example, of copolymerized N-vinylformamide. The molar masses of vinylamine polymers range, for example, from 1,000 to 10 million, preferably from 10,000 to 5 million (determined by light scattering). This molar mass range corresponds, for example, to K values of from 5 to 300, preferably from 10 to 250 (determined by the method of H. Fikentscher in 5% aqueous sodium chloride solution at 25° C. and a polymer concentration of 0.5% by weight).

The vinylamine polymers are preferably used in salt-free form. Salt-free aqueous solutions of vinylamine polymers are preparable, for example, from the above-described salt-containing polymer solutions by means of ultrafiltration using suitable membranes having molecular weight cutoffs at, for example, from 1,000 to 500,000 daltons, preferably from 10,000 to 300,000 daltons. The hereinbelow described aqueous solutions of other polymers containing amino and/or ammonium groups are likewise obtainable in salt-free form by means of ultrafiltration.

Polyethyleneimines are prepared, for example, by polymerizing ethyleneimine in an aqueous solution in the presence of acid-detaching compounds, acids or Lewis acids as catalyst. Polyethyleneimines have, for example, molar masses of up to 2 million, preferably of from 200 to 500,000. Particular preference is given to using polyethyleneimines having molar masses of from 500 to 100,000. Useful polyethyleneimines further include water-soluble crosslinked polyethyleneimines which are obtainable by reaction of polyethyleneimines with crosslinkers such as epichlorohydrin or bischlorohydrin ethers of polyalkylene glycols containing from 2 to 100 ethylene oxide and/or propylene oxide units. Also useful are amidic polyethyleneimines which are obtainable, for example, by amidation of polyethyleneimines with $C_1$- to $C_{22}$-monocarboxylic acids. Useful cationic polymers further include alkylated polyethyleneimines and alkoxylated polyethyleneimines. Alkoxylation is carried out using, for example, from 1 to 5 ethylene oxide or propylene oxide units per NH unit in the polyethyleneimine.

Useful polymers containing amino and/or ammonium groups also include polyamidoamines, which are preparable, for example, by condensing dicarboxylic acids with polyamines. Useful polyamidoamines are obtained, for example, when dicarboxylic acids having from 4 to 10 carbon atoms are reacted with polyalkylenepolyamines containing from 3 to 10 basic nitrogen atoms in the molecule. Useful dicarboxylic acids include, for example, succinic acid, maleic acid, adipic acid, glutaric acid, suberic acid, sebacic acid or terephthalic acid. Polyamidoamines may also be prepared using mixtures of dicarboxylic acids as well as mixtures of plural polyalkylenepolyamines. Useful polyalkylenepolyamines include, for example, diethylenetriamine, triethylenetetramine, tetraethylenepentamine, dipropylenetriamine, tripropylenetetramine, dihexamethylenetriamine, aminopropylethylenediamine and bisaminopropylethylenediamine. The dicarboxylic acids and polyalkylenepolyamines are heated at an elevated temperature, for example, at from 120° C. to 220° C., preferably at from 130° C. to 180° C., to prepare polyamidoamines. The water of condensation formed is removed from the system. The condensation may also employ lactones or lactams of carboxylic acids having from 4 to 8 carbon atoms. The amount of a polyalkylenepolyamine used per mole of a dicarboxylic acid is, for example, in the range from 0.8 to 1.4 mol.

Amino-containing polymers further include ethyleneimine-grafted polyamidoamines. They are obtainable from the above-described polyamidoamines by a reaction with ethyleneimine in the presence of acids or Lewis acids such as sulfuric acid or boron trifluoride etherates at, for example, from 80° C. to 100° C. Compounds of this kind are described, for example, in DE-B-24 34 816.

Useful cationic polymers also include crosslinked or uncrosslinked polyamidoamines which may additionally have been grafted with ethyleneimine prior to crosslinking. Crosslinked ethyleneimine-grafted polyamidoamines are water-soluble and have, for example, an average molar weight of from 3,000 to 1 million daltons. Customary crosslinkers include, for example, epichlorohydrin or bischlorohydrin ethers of alkylene glycols and polyalkylene glycols.

Further examples of cationic polymers that contain amino and/or ammonium groups are polydiallyldimethylammonium chlorides. Polymers of this kind are likewise known.

Useful cationic polymers further include copolymers of, for example, 1–99 mol %, preferably 30–70 mol %, of acrylamide and/or methacrylamide and 99–1 mol %, preferably 70–30 mol %, of cationic monomers such as dialkylaminoalkylacrylamide, dialkylaminoalkyl acrylate, dialkylaminoalkylmethacrylamide and/or dialkylaminoalkyl methacrylate. Basic acrylamides and methacrylamides are preferably likewise present in acid-neutralized form or in quaternized form. Examples are N-trimethylammoniumethylacrylamide chloride, N-trimethylammoniumethylmethacrylamide chloride, N-trimethylammoniumethyl methacrylate chloride, N-trimethylammoniumethyl acrylate chloride, trimethylammoniumethylacrylamide methosulfate, trimethylammoniumethylmethacrylamide methosulfate, N-ethyldimethylammoniumethylacrylamide ethosulfate, N-ethyldimethylammoniumethylmethacrylamide ethosulfate, trimethylammoniumpropylacrylamide chloride, trimethylammoniumpropylmethacrylamide chloride, trimethylammoniumpropylacrylamide methosulfate, trimethylammoniumpropylmethacrylamide methosulfate and N-ethyldimethylammoniumpropylacrylamide ethosulfate. Preference is given to trimethylammoniumpropylmethacrylamide chloride.

Further useful cationic monomers for preparing (meth) acrylamide polymers are diallyldimethylammonium halides and also basic (meth)acrylates. Useful examples are copolymers of 1–99 mol %, preferably 30–70 mol %, of acrylamide and/or methacrylamide and 99–1 mol %, preferably 70–30 mol %, of dialkylaminoalkyl acrylates and/or methacrylates such as copolymers of acrylamide and N,N-dimethylaminoethyl acrylate or copolymers of acrylamide and dimethylaminopropyl acrylate. Basic acrylates or methacrylates are preferably present in acid-neutralized form or quaternized form. Quaternization may be effected, for example, with methyl chloride or with dimethyl sulfate.

Useful polymers having amino and/or ammonium groups also include polyallylamines. Polymers of this kind are obtained by homopolymerization of allylamine, preferably in acid-neutralized form or in quaternized form, or by co-polymerizing allylamine with other monoethylenically unsaturated monomers described above as comonomers for N-vinylcarboxamides.

The cationic polymers have, for example, K values of from 8 to 300, preferably from 15 to 180 (determined by the method of H. Fikentscher in 5% aqueous sodium chloride solution at 25° C. and a polymer concentration of 0.5% by weight). At pH 4.5, for example, they have a charge density of at least 1, preferably at least 4, meq/g of polyelectrolyte.

Preferred cationic polymers are polydimethyldiallylammonium chloride, polyethyleneimine, polymers containing vinylamine units, (meth)acrylmide/basic monomer copolymers, polymers containing lysine units or mixtures thereof. Examples of preferred cationic polymers are:

polylysines of $M_w$ 250–250,000, preferably 500–100,000, and also lysine condensates having $M_w$ molar masses of from 250 to 250,000, the cocondensable component being selected, for example, from amines, polyamines, ketene dimers, lactams, alcohols, alkoxylated amines, alkoxylated alcohols and/or nonproteinogenic amino acids, vinylamine homopolymers, 1–99% hydrolyzed polyvinylformamides, copolymers of vinylformamide and vinyl acetate, vinyl alcohol, vinylpyrrolidone or acrylamide, each having molar masses of 3,000–500,000, vinylimidazole homopolymers, vinylimiazole copolymers with vinylpyrrolidone, vinylformamide, acrylamide or vinyl acetate having molar masses of from 5,000 to 500,000 and also quaternary derivatives thereof, polyethyleneimines, crosslinked polyethyleneimines or amidated polyethyleneimines having molar masses of from 500 to 3,000,000, amine-epichlorohydrin polycondensates which contain imidazole, piperazine, $C_1$–$C_8$-alkylamines, $C_1$–$C_8$-dialkylamines and/or dimethylaminopropylamine as amine component and have a molar mass of from 500 to 250,000, and polymers containing basic (meth) acrylamide or (meth)acrylate ester units, polymers containing basic quaternary (meth)acrylamide or (meth) acrylate ester units having molar masses of from 10,000 to 2,000,000.

Amino-containing polymers which have been applied as hydrophilicizers to the melamine-formaldehyde resin foams may optionally be crosslinked thereon. Crosslinking of the foams treated with polymers containing amino groups is obtained, for example, by reaction with at least bifunctional crosslinkers such as epichlorohydrin, bischlorohydrin ethers of polyalkylene glycols, polyepoxides, multifunctional esters, multifunctional acids or multifunctional acrylates.

The inventive foams based on melamine-formaldehyde resins are used in hygiene articles to acquire, distribute and immobilize body fluids, especially blood. Their hydrophilic character permits spontaneous acquisition of aqueous body fluids. The open-celled structure ensures rapid transportation into the foam interior. Hygiene articles which include the foams to be used according to the invention are essentially infant diapers, incontinence products, femcare articles, wound contact materials or secondary wound dressings.

The melamine-formaldehyde resin foams for inventive use in the hygiene sector are open-pored and hydrophilic. The droplet absorption rate of the melamine-formaldehyde foams according to the invention is less than 5 seconds, preferably less than 2 seconds, particularly preferably less than 1 second.

The open-celled resilient foams are preferably incorporated as sheet-like structures in the form of foam fleeces from 0.1 to 10 mm, preferably from 1 to 5 mm, in thickness into hygiene products such as infant diapers, incontinence and femcare articles or as wound contact materials or in dressing materials. Foam density is, for example, in the range from 5 to 200 g/l, preferably from 10 to 50 g/l. The foams preferably have a webbed structure, a BET specific surface area of more than 0.5 $m^2$/g, for example, in the range from 1 to 7 $m^2$/g, a Free Swell Capacity of more than 20 g/g, for example, from 80 to 120 g/g, and a tensile strength of >60 $J/m^2$, for example, from 100 to 600 $J/m^2$, in the wet state.

A hygiene article generally constitutes a combination of a liquid-impervious backsheet, a liquid-pervious topsheet, and an absorbent interlayer core. Hygiene articles of this type are known and described, for example, in DE-U-92 18 991 and EP-A-0 689 818. The absorbent composition is fixed between topsheet and backsheet. Elastic cuffs and self-adhesive tabs may optionally be integrated in the hygiene article. A preferred hygiene article construction is known, for example, from U.S. Pat. No. 3,860,003.

When the hydrophilic open-celled resilient foams are used in a hygiene article, there are, for example, two ways of configuring the absorbent interlayer core:

1. The melamine-formaldehyde foam layer is used as the absorbent interlayer core without further layers. It then acts simultaneously as acquisition or acquisition/distribution layer and as storage layer.
2. The absorbent interlayer core consists of (a) a melamine-formaldehyde foam layer, which acts as acquisition or acquisition/distribution layer, and (b) a storage layer containing 10–100% by weight of highly swellable hydrogel.

The storage layer either is a hydrogen layer or constitutes compositions which include highly swellable hydrogels or have them fixed to them. Any composition is suitable that is capable of accommodating highly swellable hydrogels and being integrated into the absorbent core. A multiplicity of such compositions is already known and described in detail in the literature. A composition for installing the highly swellable hydrogels can be, for example, a fiber matrix consisting of a cellulose fiber mixture (airlaid web, wet laid web) or of synthetic polymer fibers (meltblown web, spun-bonded web), or else of a fiber blend of the cellulose fibers and synthetic fibers. Furthermore, open-pored foams or the like may be used to install highly swellable hydrogels.

Alternatively, such a composition can be the result of fusing two individual layers to form one or, better, a multiplicity of chambers which contain the highly swellable hydrogels. In this case, at least one of the two layers should be water-pervious. The second layer may be either water-pervious or water-impervious. The layer material used may be tissues or other fabrics, closed or open-celled foams, perforated films, elastomers or fabrics composed of fiber material. When the storage layer consists of a composition of layers, the layer material should have a pore structure whose pore dimensions are small enough to retain the highly swellable hydrogel particles. The above examples on the composition of the storage layer also include laminates composed of at least two layers between which the highly swellable hydrogels can be installed and fixed.

Furthermore, the storage layer can consist of a carrier material, for example, a polymer film. on which the highly swellable hydrogel particles are fixed. The fixing can be effected not only on one side but also on both sides. The carrier material can be water-pervious or water-impervious.

In the above compositions of the storage layer, the highly swellable hydrogels can have a weight fraction of from 10 to 100% by weight, preferably from 40 to 100% by weight and particularly preferably from 70 to 100% by weight. When the above storage layer composition constitutes a fiber matrix, then the absorbent composition results from a mixture of fiber materials and highly swellable hydrogels.

The storage layer may contain manifold fiber materials, which are used as fiber network or matrices. The present invention encompasses not only fibers of natural origin (modified or unmodified) but also synthetic fibers.

Examples of cellulose fibers include cellulose fibers which are customarily used in absorption products, such as fluff pulp and pulp of the cotton type. The materials (hard- or softwoods), production processes, such as chemical pulp, semi-chemical pulp, chemothermomechanical pulp (CTMP) and bleaching processes, are not particularly restricted. For example, natural cellulose fibers such as cotton, flax, silk, wool, jute, ethylcellulose and cellulose acetate are used.

Suitable synthetic fibers are produced from polyvinyl chloride, polyvinyl fluoride, polytetrafluoroethylene, polyvinylidene chloride, polyacrylic compounds such as ORLON®, polyvinyl acetate, polyethyl vinyl acetate, soluble or insoluble polyvinyl alcohol. Examples of synthetic fibers include thermoplastic polyolefin fibers, such as polyethylene fibers (PULPEX®), polypropylene fibers and poly-ethylene-polypropylene bicomponent fibers, polyester fibers, such as polyethylene terephthalate fibers (DACRON® or KODEL®), copolyesters, polyvinyl acetate, polyethyl vinyl acetate, polyvinyl chloride, polyvinylidene chloride, polyacrylics, polyamides, copolyamides, polystyrene and copolymers of the aforementioned polymers and also bicomponent fibers composed of polyethylene terephthalate-polyethyleneisophthalate copolymer, polyethyl vinyl acetate/polypropylene, polyethylene/polyester, polypropylene/polyester, copolyester/polyester, polyamide fibers (nylon), polyurethane fibers, polystyrene fibers and polyacrylonitrile fibers. Preference is given to polyolefin fibers, polyester fibers and their bicomponent fibers. Preference is further given to thermally adhesive bicomponent fibers composed of polyolefin of the core-sheath type and side-by-side type on account of their excellent dimensional stability following fluid absorption.

The synthetic fibers mentioned are preferably used in combination with thermoplastic fibers. In the course of the heat treatment, the latter migrate to some extent into the matrix of the fiber material present and so constitute bond sites and renewed stiffening elements on cooling. Additionally the addition of thermoplastic fibers means that there is an increase in the present pore dimensions after the heat treatment has taken place. This makes it possible, by continuous addition of thermoplastic fibers during the formation of the absorbent core, to continuously increase the fraction of thermoplastic fibers in the direction of the topsheet, which results in a similarly continuous increase in the pore sizes. Thermoplastic fibers can be formed from a multiplicity of thermoplastic polymers which have a melting point of less than 190° C., preferably in the range from 75° C. to 175° C. These temperatures are too low for damage to the cellulose fibers to be likely.

The above-described synthetic fibers may, for example, be from 1 to 200 mm in length and from 0.1 to 100 denier (gram per 9,000 meters) in diameter. Preferred thermoplastic fibers are from 3 to 50 mm in length, particularly preferred thermoplastic fibers are from 6 to 12 mm in length. The preferred diameter for the thermoplastic fiber is in the range from 1.4 to 10 decitex, and the range from 1.7 to 3.3 decitex (gram per 10,000 meters) is particularly preferred. The form of the fiber may vary; examples include woven types, narrow cylindrical types, cut/chopped yarn types, staple fiber types and continuous filament fiber types.

The fibers in the absorbent composition of the. invention can be hydrophilic and/or hydrophobic. According to the definition of Robert F. Gould in the 1964 American Chemical Society publication "Contact angle, wettability and adhesion," a fiber is referred to as hydrophilic when the contact angle between the liquid and the fiber (or the fiber surface) is less than 90° or when the liquid tends to spread spontaneously on the same surface. The two processes are generally coexistent Conversely, a fiber is termed hydrophobic when a contact angle of greater than 90° is formed and no spreading is observed.

Preference is given to using hydrophilic fiber material. Particular preference is given to using fiber material which is weakly hydrophilic on the body side and most hydrophilic in the region surrounding the highly swellable hydrogels. In the manufacturing process, layers having different hydrophilicities are used to create a gradient which channels impinging fluid to the hydrogel, where it is ultimately absorbed.

Suitable hydrophilic fibers for use in the absorbent core of the invention include, for example, cellulose fibers, modified cellulose fibers, rayon, polyester fibers, for example, polyethylene terephthalate (DACRON®), and hydrophilic nylon (HYDROFIL®). Suitable hydrophilic fibers may also be obtained by hydrophilicizing hydrophobic fibers, for example, the treatment of thermoplastic fibers obtained from polyolefins (e.g., polyethylene or polypropylene, polyamides, polystyrenes, polyurethanes, etc.) with surfactants or silica. However, for cost reasons and ease of availability, cellulosic fibers are preferred.

The highly swellable hydrogel particles are embedded into the fiber material described. This can be done in various ways, for example, by using the hydrogel material and the fibers together to create an absorbent layer in the form of a matrix, or by incorporating highly swellable hydrogels into fiber mixture layers, where they are ultimately fixed, whether by means of adhesive or lamination of the layers.

The fluid-acquiring and distributing fiber matrix may comprise synthetic fiber or cellulosic fiber or a mixture of synthetic fiber and cellulosic fiber, in which case the mixing ratio may vary from (100 to 0) synthetic fiber:(0 to 100) cellulosic fiber. The cellulosic fibers used may additionally have been chemically stiffened to increase the dimensional stability of the hygiene article.

The chemical stiffening of cellulosic fibers may be provided in different ways. A first way of providing fiber stiffening is by adding suitable coatings to the fiber material. Such additives include, for example, polyamide-epichlorohydrin coatings (KYMENE® 557 H), polyacrylamide coatings (described in U.S. Pat. No. 3, 556,932 or as the PAREZ® 631 NC commercial product), melamine-formaldehyde coatings and polyethyleneimine coatings.

Cellulosic fibers may also be chemically stiffened by chemical reaction. For instance, suitable crosslinker substances may be added to effect crosslinking taking place within the fiber. Suitable crosslinker substances are typical substances used for crosslinking monomers including but not limited to $C_2$–$C_8$-dialdehydes, $C_2$–$C_8$-monoaldehydes having acid functionality and in particular $C_2$–$C_9$polycarboxylic acids. Specific substances from this series are, for example, glutaraldehyde, glyoxal, glyoxylic acid, formaldehyde and citric acid. These substances react with at least 2 hydroxyl groups within any one cellulose chain or between two adjacent cellulose chains within any one cellulose fiber. The crosslinking causes a stiffening of the fibers, to which greater dimensional stability is imparted as a result of this treatment. In addition to their hydrophilic character, these fibers exhibit uniform combinations of stiffening and elasticity. This physical property makes it possible to retain the capillary structure even under simultaneous contact with fluid and compressive forces and to prevent premature collapse.

Chemically crosslinked cellulose fibers are known, cf., for example, WO-A-91/11162. The chemical crosslinking imparts stiffening to the fiber material, which is ultimately reflected in improved dimensional stability for the hygiene article as a whole. The individual layers are joined together by methods known to one skilled in the art, for example, by intermelting by heat treatment, addition of hot-melt adhesives, latex binders, etc.

Generally, the invention utilizes a hydrophilicized fleece of an open-celled resilient melamine-formaldehyde resin foam having very low formaldehyde emissions as or in the absorbent interlayer core. The dimension (thickness) of the absorbent interlayer when used as an absorbent core is generally in the range from 0.5 to 10 mm, preferably in the range from 1 to 5 mm. When used as an acquisition and distribution layer in combination with a storage layer, the thickness is in the range from 0.1 to 10 mm, preferably in the range from 0.5 to 3 mm.

The topsheet can be produced in various ways, for example, as a woven, nonwoven, spun or combed fiber mixture. Preference is given to using a combed fiber mixture which is thermally bonded to form the topsheet. The basis weight of the topsheet is preferably in the range from 18 to 25 g/m². It has a tensile strength of at least 400 g/cm in the dry state and 55 g/cm in the wet state.

The backsheet is usually a liquid-impervious material, for example, polyolefin (a polyethylene backsheet, for example) to protect the user's clothing from possible leakage.

The individual layers from which the hygiene articles are constructed are joined together by known methods, for example, by intermelting the layers by heat treatment, addition of hot-melt adhesives, latex binders, etc. The absorbent interlayer core is positioned between topsheet and backsheet.

Methods of Measurement

Droplet Absorption Rate

A single droplet of a 0.9% sodium chloride solution is pipetted onto a foam layer about 5 mm in thickness and the time taken for the droplet to disappear into the foam is recorded. The foam was rated hydrophilic when the absorption time was <5 sec.

Density

Any suitable gravimetric method can be used for determining the density of the foam. What is determined is the mass of solid foam per unit volume of foam structure. A method for density determination of the foam is described in ASTM Method No. D 3574-86, Test A. This method was originally developed for the density determination of urethane foams, but can also be used for this purpose. By this method, the dry mass and volume of a preconditioned sample is determined at 22° C.±2° C. Volume determinations of larger sample dimensions are carried out under atmospheric pressure.

Free Swell Capacity (FSC)

This method is used to determine the free swellability of the open-celled resilient melamine-formaldehyde foam. To determine FSC, a testpiece of suitable size, for example, with an area of approximately 1 cm×1 cm, is cut out of a foam blank and weighed. The testpiece is placed in an excess of 0.9% NaCl solution (at least 0.83 l of sodium chloride solution/1 g of foam) for 30 minutes. The testpiece is subsequently allowed to drip for 10 minutes before it is hung up by one corner, avoiding compression at all costs. The amount of liquid absorbed is determined by weighing the testpiece.

Acquisition Time

The open-celled resilient melamine-formaldehyde foam is cut into layers 1.5 or 2 or 4 mm in thickness. A commercially available diaper is carefully cut open, the highloft used as acquisition medium removed and instead the open-celled resilient melamine-formaldehyde foam layer inserted. The diaper is resealed. Synthetic urine solution is applied to it through a plastic plate having a ring in the middle (inner diameter of the ring 6.0 cm, height 4.0 cm). The plate is loaded with additional weights so that the total load on the diaper is 13.6 g/cm². The plastic plate is placed on the diaper in such a way that the center of the diaper is also the center of the application ring. 60 ml of 0.9% by weight sodium chloride solution are applied three times. The sodium chloride solution is measured in a graduated cylinder and applied to the diaper in a continuous stream through the ring in the plate. At the same time, the time taken for the solution to penetrate completely into the diaper is recorded. The time measured is noted as acquisition time 1. Thereafter, the diaper is loaded with a plate for 20 min, the load being maintained at 13.6 g/cm². This is followed by the second application of the liquid. The time measured is noted as acquisition time 2. The same method is employed to determine acquisition time 3.

Specific Surface Area

Specific surface area is determined by the BET method as set forth in DIN 66132.

Formaldehyde Emission

Determined by Edana method 210.1–99 (testing to EU standard EN ISO 14184-1)

One g of the foam sample to be tested is cut into small pieces, introduced into an Erlenmeyer flask together with 100 ml of water and tightly sealed. The Erlenmeyer flask is placed into a water bath maintained at 40° C. and is left therein for 60 min with periodic shaking. Subsequently, the solution obtained is filtered off or the foam is expressed.

The formaldehyde content of the solution obtained is determined by the acetylacetone method.

Unless the context suggests otherwise, the percentages in the examples are by weight.

EXAMPLES

Comparative Example 1

Seventy-five parts of a spray-dried melamine-formaldehyde precondensate (molar ratio 1:3) were dissolved in 25 parts of water. This resin solution was admixed with 3% of formic acid, 2% of a sodium $C_{12}/C_{18}$-alkanesulfonate and 19% of pentane, each based on the resin. The mixture was vigorously stirred and subsequently foamed in a polypropylene foaming mold by irradiation with microwave energy at 2.54 GHz. The foam was dried at 100° C. and subsequently conditioned at 220° C. for 30 min. The melamine-formaldehyde foam thus prepared was hydrophilic and had a density of 10 g/l. Formaldehyde emissions after 1 h of storage in water at 40° C. were 150 mg of formaldehyde/kg of foam. The teabag test Free Swell Capacity (FSC) was 103 g/g. The foam had a BET specific surface area of 5.3 m²/g.

Comparative Example 2

Seventy parts of a spray-dried melamine-formaldehyde precondensate (molar ratio 1:1.6) were dissolved in 30 parts of water. This resin solution was admixed with 3% of an emulsifier mixture of an alkanolamide and an ethoxylated fatty alcohol and also with 3% of formic acid and 10% of pentane. The mixture was foamed, and the foam dried and conditioned, as described in comparative example 1. The foam thus prepared was hydrophobic and its density was likewise 10 g/l. Formaldehyde emissions were less than 20 mg of formaldehyde/kg of foam.

Inventive Examples 1 to 15

The foam prepared according to comparative example 2 was cut into layers 5 mm in thickness, which were placed in 1% aqueous solutions of the coatings reported in table 1 and completely wetted by flexing. Each foam sample was removed from the solution after 30 min, squeezed off and predried in air for about 18 hours. The samples. were subsequently dried at 110° C. under reduced pressure for 1 hour. Thereafter, all the treated foam samples were hydrophilic, cf. Table 1.

Preparation of Surfactant 1

A 53% aqueous solution of a polyethyleneimine (121 g) having a number average molecular weight of about 5000 was dewatered at 120° C. and 25 mbar. At 80° C. the polyethyleneimine, which was stirred under nitrogen, was admixed with 15.5 g of $C_{12}$–$C_{14}$-fatty acid (acid number 271 g of KOH/g) (EDENOR® C 12 70, from Henkel). After heating, the batch was stirred at 160° C. for 6 hours. The water of reaction formed was distilled off. After cooling to 140° C., 51.8 g of formic acid were added dropwise and the batch was subsequently stirred at 140° C. for 4.5 hours. After the amidation had ended, the batch was cooled down to 90° C. and admixed with 230 ml of completely ion-free water with stirring to provide 332 g of a 31.5% aqueous solution of a polyethyleneimine amidated 5.0% with $C_{12}$–$C_{14}$-fatty acid and exhaustively with formic acid.

Preparation of Surfactant 2

In a four-neck flask equipped with stirrer, dropping funnel, thermometer and reflux condenser, 20.0 g (0.1 mol) of bis(aminopropyl)piperazine were dissolved in 200 g of acetone. 22.2 g (0.1 mol) of isophorone diisocyanate were added dropwise in such a way that the temperature did not rise above 30° C. The reaction mixture was refluxed for a further hour and then admixed with 110 g of HCl (1 N) and 100 g of water. The acetone was then. distilled off under reduced pressure to leave a polyurea solution having a solids content of 16.7% by weight and a pH of 7.2.

Measuring conditions of the K values for the polymers mentioned in Table 1:

| Polymer | Solvent | Polymer concentration of solution [% by weight] | pH of solution |
| --- | --- | --- | --- |
| Polyvinylamine | 3% aqueous NaCl solution | 0.5 | 11.0 |
| Polyacrylic acid | Water | 1.0 | 7.0 (neutralized with NaOH) |
| Polylysine | Water | 1.0 | 10.3 |
| Copolymer of acrylamide and vinylimidazole | 3% aqueous NaCl solution | 0.1 | 8.0 |
| Copolymer of acrylamide and N-trimethyl-ammoniumethyl acrylate chloride | 3% aqueous NaCl solution | 0.1 | 4.8 |

TABLE 1

| Example | Coating | Hydrophilic | Hydrophobic |
| --- | --- | --- | --- |
| Comp. 1 | — | X | |
| Comp. 2 | — | | X |
| Inv. 1 | Diglycerol monooleate | X | |
| Inv. 2 | Sorbitan monooleate | X | |
| Inv. 3 | Reaction product of an unsaturated $C_{13}C_{15}$ oxo alcohol with 4 ethylene oxide units and 4 propylene oxide units | X | |
| Inv. 4 | Mixture of 25% of stearyl alcohol and 75% of a reaction product of cetylstearyl alcohol with 6 ethylene oxide units | X | |
| Inv. 5 | Polyacrylic acid, K value 110 | X | |
| Inv. 6 | Polyvinylamine, K value 90 | X | |
| Inv. 7 | N-Methylaminopropyltri-methoxysilane | X | |
| Inv. 8 | Amino-modified silicone-polyether copolymer, NUWET ® 300 from OSi | X | |
| Inv. 9 | Polyalkylene oxide-modified polydimethylsiloxane, Nuwet 500 from OSi | X | |
| Inv. 10 | Organo-modified polymethylsiloxane, NUWET ® 100 from OSi | X | |
| Inv. 11 | Reaction mixture of poly-vinylamine (K value 90) and ethylene glycol diglycidyl ether in weight ratio of 40/1 | X | |
| Inv. 12 | Copolymer of acrylamide and vinylimidazole having a molar ratio of 1/1, K value 30 | X | |
| Inv. 13 | Copolymer of acrylamide and N—trimethyl—ammoniumethyl acrylate chloride having a molar ratio of 1/1, K value 30 | X | |
| 14 | Surfactant 1 | X | |
| 15 | Surfactant 2 | X | |

Inventive Example 16

The melamine-formaldehyde resin foam hydrophilicized according to inventive example 10 was cut into layers 2 mm in thickness. A commercially available diaper was carefully cut open, the highloft removed and instead the 2 mm thick foam layer inserted into the diaper. The diaper was then resealed and the times taken to absorb 3 successive additions of 60 ml of synthetic urine were recorded The measured values are reported in Table 2.

Inventive Example 17

Inventive example 16 was repeated except that a foam hydrophilicized according to inventive example 6 was incorporated into a diaper arid. the acquisition times were measured. The results are reported in Table 2.

Comparative Example 3

A commercially available diaper was carefully cut open, the highloft removed and then reinserted and the diaper resealed. This procedure was intended to ensure optimum comparability. The acquisition times were then determined. The results are reported in Table 2.

Comparative Example 4

The low-formaldehyde foam of melamine-formaldehyde condensate prepared according to comparative example 2 was incorporated into a diaper as described in inventive example 16. The acquisition times were then determined. The results are reported in Table 2.

Comparative Example 5

The foam of melamine-formaldehyde condensate prepared according to comparative example 1 was incorporated into a diaper as described in inventive example 16. The acquisition times were then determined. The results are reported in Table 2.

TABLE 2

| Diaper | Time to absorb first 60 ml [sec] | Time to absorb second 60 ml [sec] | Time to absorb third 60 ml [sec] |
|---|---|---|---|
| Comparative example 3 | 7 | 19 | 29 |
| Comparative example 4 | 80 | 125 | 148 |
| Comparative example 5 | 3 | 6 | 8 |
| Inventive Example 16 | 3 | 4 | 6 |
| Inventive Example 17 | 4 | 6 | 8 |

Table 2 reveals that the acquisition of the low-formaldehyde foam hydrophilicized are significantly better than those of a commercially available diaper and equivalent to those of the original, high-formaldehyde foam of comparative example 1.

What is claimed is:

1. Hydrophilic open-celled resilient foams comprising melamine-formaldehyde resins, characterized by a droplet absorption rate of less than 5 seconds and an EU standard EN ISO 14184-1 formaldehyde emission of less than 100 mg of formaldehyde/kg of foam.

2. The hydrophilic open-celled resilient foams as claimed in claim 1, characterized by a density of from 5 to 200 g/l, a specific surface area (determined according to BET) of more than 0.5 $m^2$/g and a Free Swell Capacity of more than 20 g/g.

3. The hydrophilic open-celled resilient foams as claimed in claim 1 or 2, characterized by a tensile strength of >60 $J/m^2$ in the wet state.

4. A process for preparing hydrophilic open-celled resilient foams as claimed in claim 1 which comprises (a) heating an aqueous solution or dispersion comprising a melamine-formaldehyde precondensate, an emulsifier, a blowing agent and a curing agent to form a foam and crosslink the precondensate, (b) then conditioning the foam at from 120° C. to 300° C. for from 1 to 180 minutes to remove volatiles, and (c) treating the foam during the conditioning or thereafter with at least one hydrophilicizer and/or with ozone, a corona discharge or a plasma.

5. The process as claimed in claim 4, wherein the melamine-formaldehyde precondensate has a molar ratio of melamine to formaldehyde in the range from 1:1.0 to 1:1.9.

6. The process as claimed in claim 4, wherein the melamine-formaldehyde precondensate used has a molar ratio of melamine to formaldehyde in the range from 1:1.3 to 1:1.8.

7. The process as claimed in claim 4, wherein the hydrophilicizer comprises at least one surfactant.

8. The process as claimed in claim 4, wherein the hydrophilicizer comprises a polymer containing amino and/or ammonium groups.

9. The process as claimed in claim 4, wherein the hydrophilicizer comprises a polyalkylene glycol, a polymer of monoethyleneically unsaturated carboxylic acids, or a mixture thereof.

10. The process as claimed in claim 8, wherein the hydrophilicizer comprises a polymer containing vinylamine units, a polyethyleneimine, or a mixture thereof.

11. Hydrophilic open-celled resilient foams prepared by the process of claim 4.

12. A method of acquiring, distributing, and immobilizing body fluids comprising contacting the body fluid with a hydrophilic open-celled resilient foam of claim 1.

13. A hygiene article to acquire, distribute, and immobilize body fluids comprising a hydrophilic open-celled resilient foam of claim 1.

14. The article of claim 13, wherein article is selected from the group consisting of infant diapers, incontinence products, femcare articles, wound contact materials and secondary wound dressings.

* * * * *

UNITED STATES PATENT AND TRADEMARK OFFICE
CERTIFICATE OF CORRECTION

PATENT NO. : 6,800,666 B2
DATED : October 5, 2004
INVENTOR(S) : Hähnle et al.

It is certified that error appears in the above-identified patent and that said Letters Patent is hereby corrected as shown below:

<u>Title page,</u>
Item [54], Title, reads "MELAMINE/FORMALDEHYDE"
should be -- MELAMINE FORMALDEHYDE --

<u>Column 20,</u>
Line 4, "1to" should be -- 1 to --
Line 39, "wherein article" should be -- wherein the article --

Signed and Sealed this

Third Day of May, 2005

JON W. DUDAS
*Director of the United States Patent and Trademark Office*